(12) United States Patent
Kumar et al.

(10) Patent No.: US 6,528,660 B1
(45) Date of Patent: Mar. 4, 2003

(54) PROCESS FOR THE PRODUCTION OF AMORPHOUS ATORVASTATIN CALCIUM

(75) Inventors: Yatendra Kumar, Haryana (IN); Rajesh Kumar Thaper, Haryana (IN); S. M. Dileep Kumar, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/979,475

(22) PCT Filed: Jan. 6, 2000

(86) PCT No.: PCT/IB00/00014

§ 371 (c)(1),
(2), (4) Date: Feb. 12, 2002

(87) PCT Pub. No.: WO00/71116

PCT Pub. Date: Nov. 30, 2000

(30) Foreign Application Priority Data

May 25, 1999 (IN) .......................... 75/DEL/99

(51) Int. Cl.[7] .......................... C07D 207/327
(52) U.S. Cl. .......................... 548/537
(58) Field of Search .......................... 548/537

(56) References Cited

U.S. PATENT DOCUMENTS

| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,248,793 A | 9/1993 | Millar et al. |
| 5,273,995 A | 12/1993 | Roth |
| 5,280,126 A | 1/1994 | Butler et al. |
| 5,342,952 A | 8/1994 | Butler et al. |

FOREIGN PATENT DOCUMENTS

| DE | 33 27 449 A1 | 7/1983 |
| WO | WO 97/03958 | 2/1997 |
| WO | WO 97/03959 | 2/1997 |
| WO | WO 97/03960 | 2/1997 |

*Primary Examiner*—Joseph K. McKane
*Assistant Examiner*—Sonya N. Wright
(74) *Attorney, Agent, or Firm*—Jayadeep R. Deshmukh, Esq.

(57) ABSTRACT

A process for the preparation of amorphous atorvastatin calcium and hydrates thereof which comprises: (a) dissolving crystalline atorvastatin calcium in a non-hydroxylic solvent; (b) adding a non-polar hydrocarbon anti-solvent or adding the dissolved atorvastatin to the non-polar anti-solvent to precipitate out atorvastatin calcium; and (c) removing the solvent by filtration to afford amorphous atorvastatin calcium.

5 Claims, 2 Drawing Sheets

PROCESS FOR THE PRODUCTION OF AMORPHOUS ATORVASTATIN CALCIUM

This application is a 371 of PCT/IB00/00014 filed Jan. 6, 2000.

FIELD OF THE INVENTION

The present invention relates to a process for the production of amorphous atorvastatin calcium.

BACKGROUND OF THE INVENTION

Atorvastatin is chemically [R-(R*,R*)]-2-(4-fluorophenyl)-β dihydroxy-5-(1-methylethyl)-3-phenyl 4-[(phenylamino)carbonyl]-1H pyrrole-1-heptanoic acid. Atorvastatin calcium, a synthetic HMG-CoA reductase inhibitor, is used for the treatment of hyperlipidemia and hypercholesterolemia, both of which are risk factors for arteriosclerosis and coronary heart disease. Open dihydroxy carboxylic acid, lactone and various salt forms of atorvastatin have been synthesized.

U.S. Pat. 5,273,995, describes that R-form of the ring opened acid form has surprising inhibition of the biosynthesis of cholesterol. Atorvastatin in its calcium salt form, i.e. [R-(R*,R*)]-2-(4-fluoro-phenyl)-β,δ-dihydroxy-5-(1-methylethyl)-3-phenyl-4-[(phenylamino)carbomyl]-1H-pyrrole-1-heptanoic acid calcium salt (2:1) having Formula 1:

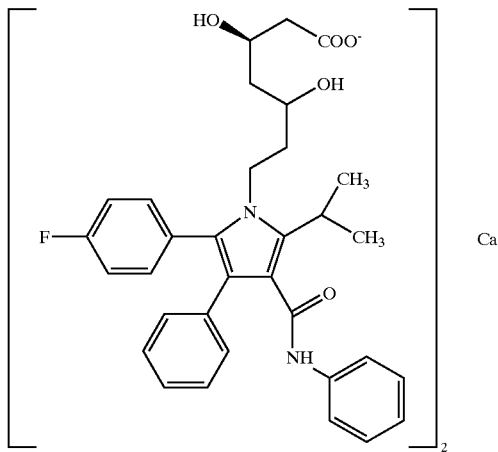

is more suited to formulations and has been recommended as a drug.

U.S. Pat. Nos. 5,003,080; 5,097,045; 5,103,024; 5,124,482; 5,149,837; 5,248,793; 5,280,126; 5,342,952, which are herein incorporated by reference, describe various processes and key intermediates for preparing at orvastatin.

Atorvastatin calcium produced by the processes described in the above mentioned United States patents does not give amorphous atorvastatin consistently but gives a mixture of its crystalline and amorphous forms, which has unsuitable filtration and drying characteristics and are not suitable for large-scale production.

PCT application, WO 97/03959, discloses novel crystalline forms of atorvastatin calcium designated as Form I, Form II, and Form IV and method for their preparation which provide more favourable filtration and drying characteristics.

PCT application WO 97/03960 describes a procedure for converting the crystalline form of atorvastatin to the amorphous form. Process disclosed therein comprises dissolving crystalline form-I atorvastatin in a non-hydroxylic solvent like tetrahydrofuran or mixtures of tetrahydrofuran and toluene. The process involves complete removal of the solvent under high temperature (about 90° C.) and high vacuum (about 5 mm) using capital intensive equipment. Exposure of the material to high temperature for several days leads to degradation of the product. This makes the process very inconvenient to operate at a large scale. Slow removal of solvents at a manufacturing scale renders this process as inefficient cost-wise and less productive.

SUMMARY OF THE INVENTION

It is an objective of the present invention to provide an efficient process for the production of amorphous atorvastatin, which eliminates the problems of prior art and is convenient to operate on a commercial scale.

Accordingly, the present invention provides a process for the preparation of atorvastatin calcium in an amorphous form which comprises dissolving crystalline atorvastatin in a non-hydroxylic solvent, adding a suitable non-polar hydrocarbon solvent and recovering atorvastatin from a solution thereof, by solvent precipitation, isolating and drying the product.

Generally, the product can be isolated by any standard method known in the art such as by filtration, centrifugation or decantation. Typically, this product is isolated by filtration when any of the solvents within the scope of the process are used.

Major advantages of the present invention compared to the prior art processes are:
  i. elimination of the need to remove solvent by drying techniques.
  ii. less time consuming with improved filtration.
  iii. easy to operate on large-scale.
  iv. reproducibly produces amorphous product having allowable levels of residual solvents.

The present invention thus provides a novel process for the preparation of amorphous atorvastatin calcium and hydrates thereof which comprises:

(a) dissolving crystalline atorvastatin calcium in a non-hydroxylic solvent;
  (b) adding a non-polar hydrocarbon anti-solvent to precipitate out the material; and
  (c) removing the solvent by filtration to afford amorphous atorvastatin calcium The non-hydroxylic solvent is selected from a group of solvents, which have the ability to dissolve crystalline atorvastatin and includes tetrahydrofuran. Suitable non-polar hydrocarbon solvents are selected from a group consisting of: n-hexane, n-heptane, cyclohexane, hexane fraction, heptane fraction or the like. In a preferred embodiment of this invention, the non-hydroxylic solvent is tetrahydrofuran and anti-solvent is n-hexane, cyclohexane or n-heptane.

Generally, crystalline atorvastatin calcium is dissolved in a non-hydroxylic solvent, e.g. tetrahydrofuran, at a concentration of about 15% w/v to about 40% w/v, preferably at a concentration of about 25% w/v to about 15% w/v at ambient temperature and a non-polar hydrocarbon, preferably n-hexane, cyclohexane or n-heptane, is added at 0° C. to 50° C., preferably at 20° C. to 25° C. The product is recovered by filtration at ambient temperature. Filtration, which is fast and smooth, is carried out using nutsche filtration or centrifuge filtration. Preferably, nutsche filtration is used on large scale preparation. Filtered material, a semi-dry powder, is further dried to remove surface solvents in a vacuum tray drier, tray drier, fluid bed drier or a rotary vacuum drier to afford amorphous material. Preferably, material is dried in a vacuum tray drier at about 20° C. to about 80° C. for 6 hours to 24 hours. Most preferably, drying is carried out at about 50° C. to about 60° C. for 12 hours.

Quantity of antisolvent varies from 5 times to 50 times the input of crystalline atorvastatin calcium depending upon its solution in non-hydroxylic solvent. Preferably, the quantity of antisolvent used is about 20 times to about 40 times the input of crystalline atorvastatin calcium to make overall concentration of about 5% w/v to about 2.5 w/v %.

Amorphous atorvastatin calcium prepared according to the process of the present invention may be characterized by its x-ray powder diffration pattern (FIG. 2) as shown in the accompanied drawings. X-ray powder diffration patterns (FIG. 2) show no peaks which are characteristic of a crystalline atorvastatin calcium (FIG. 1 of the accompanied drawings) thus demonstrating the amorphous nature of the product.

The present invention is illustrated by the following examples, which are not intended to limit the effective scope of the claims.

DETAILED DESCRIPTION OF THE INVENTION

EXAMPLE 1

[R-(R*,R*)2-(4-fluorophenyl)-β,δ-dihydroxy-5-(1-methylethyl)-3-phenyl-4-[(phenylamino)carbonyl)-1H-pyrrole-1-heptanoic acid hemicalcium salt (Amorphous Atorvasatin Calcium)

Method A

Figure 1:
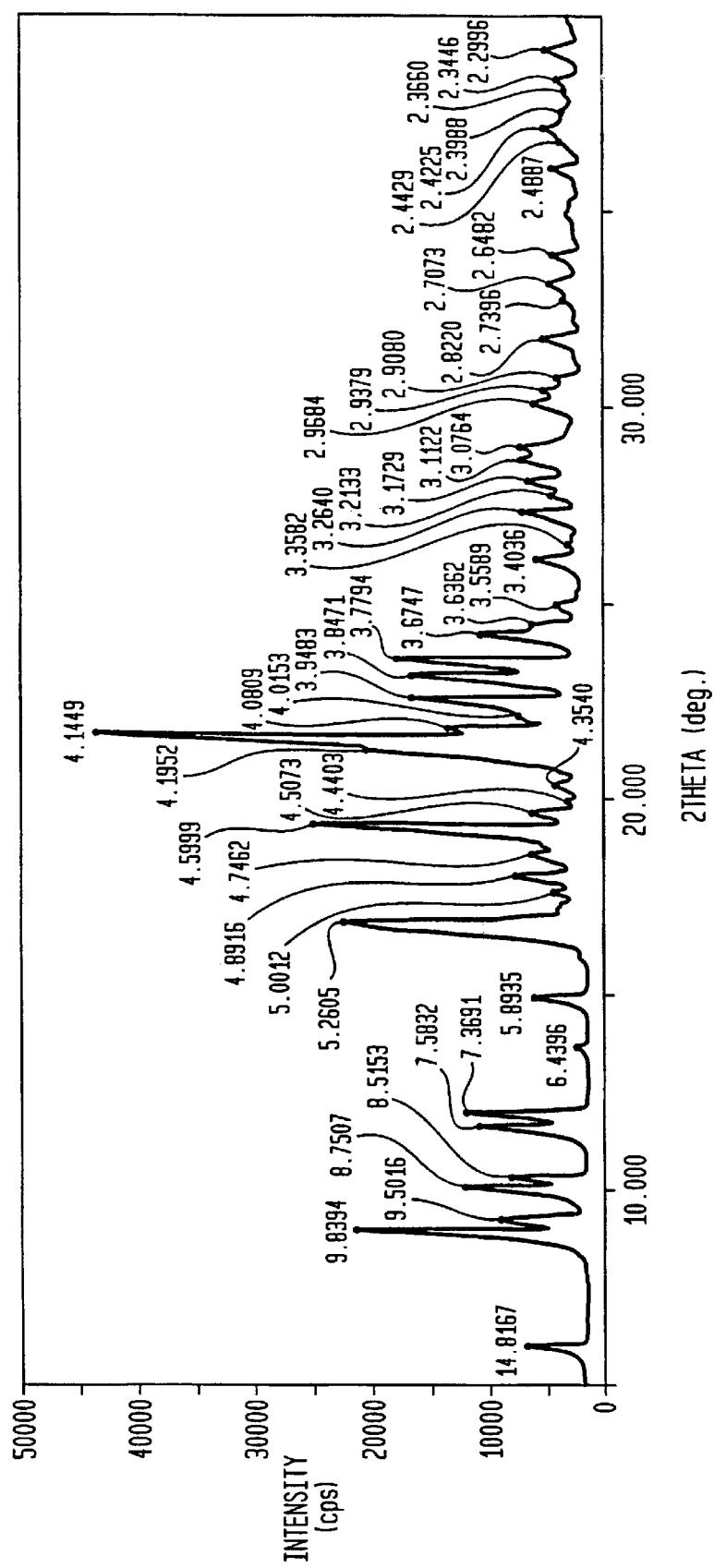
FIG. 1 is the diffractogram of crystalline atorvastatin calcium. The horizontal axis represents 2θ and the vertical axis corresponds to peak intensity.
Figure 2:
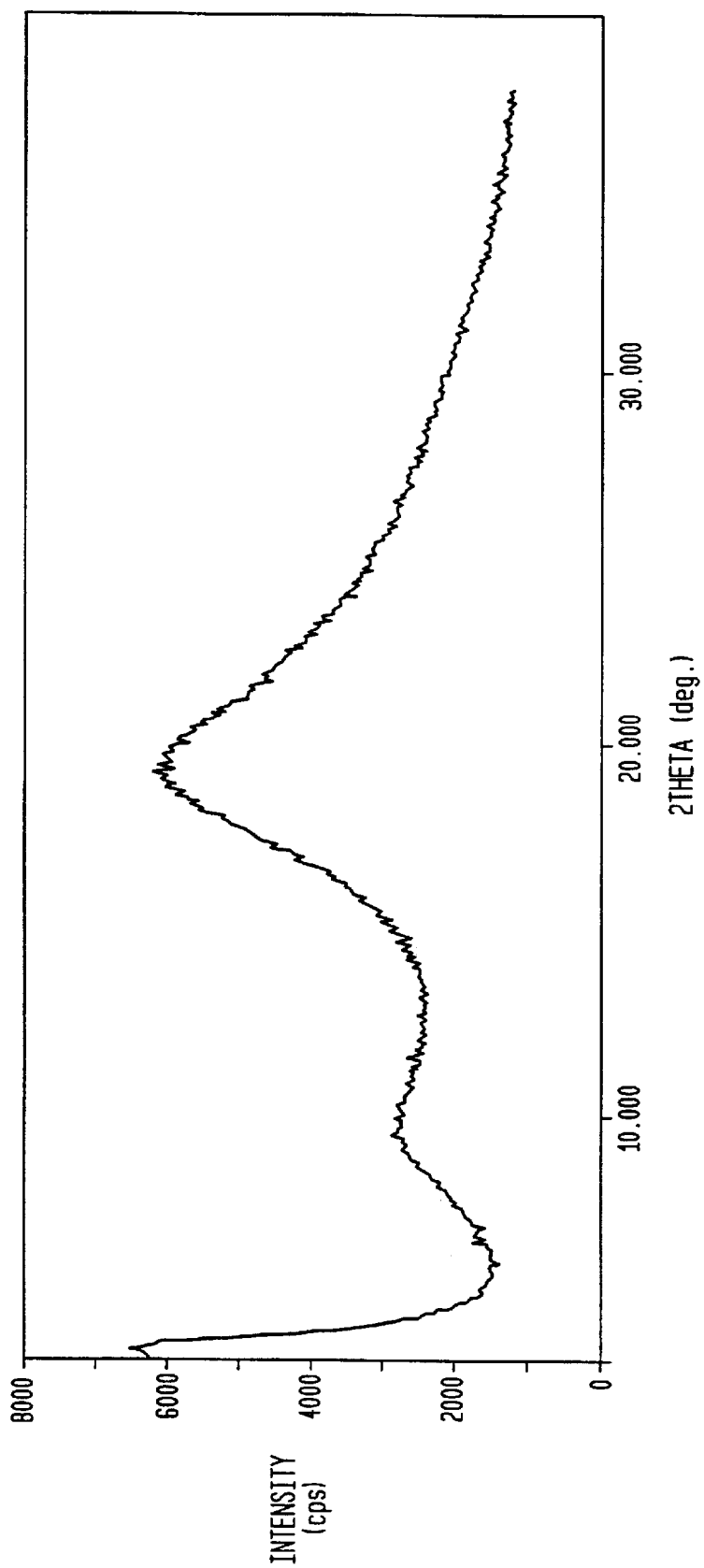
FIG. 2 is diffractogram of amorphous atorvastatin calcium. The horizontal axis represents 2θ and the vertical axis corresponds to peak intensity.

Crystalline atorvastatin calcium (10 kg) was dissolved in tetrahydrofuran (30 lt) under stirring at ambient temperature. Clear solution so obtained was added slowly to cyclohexane (350 lt) under nitrogen atmosphere. It was vigorously stirred maintaining temperature at 20–25° C. The precipitated product was centrifuged and dried under vacuum at about 60° C. for 12 hours. Atorvastatin (9.5 kg) in an amorphous form was obtained having residual solvent levels of 0.01% w/w tetrahydrofuran and 0.6% w/w cyclohexane. X-ray powder diffraction pattern (FIG. 2 as shown in the accompanied drawings) demonstrate the amorphous nature of the product.

Method B

Crystalline atorvastatin calcium (10 kg) was dissolved in tetrahydrofuran (30 lt) under stirring at ambient temperature. To a clear solution of atorvastatin, cyclohexane (350 lt) was added under vigorous stirring at 20 to 25° C. The precipitated mass was further stirred for 30 minutes and filtered in a centrifuge. The product was dried under vacuum at about 60° C. for 12 hours. Atorvastatin (9.6 kg) in an amorphous form was obtained having residual solvent levels of 0.01% w/w for tetrahydrofuran and 0.7% w/w for cyclohexane. X-ray powder diffraction pattern demonstrates the amorphous nature of the product.

EXAMPLE 2

[R-(R*,R*)-2-(4-fluorophenyl)β,δ-dihydroxy-5-(1-methylethyl)-3-phenyl-4-[(phenylamino)carbonyl)-1H-pyrrole-1-heptanoic acid hemicalcium salt (Amorphous Atorvasatin Calcium)

The process of Example 1 was repeated with crystalline atorvastatin calcium (10 kg) dissolved in tetrahydrofuran (30 lt) and using n-hexane instead of cyclohexane to give amorphous atorvastatin (9.5 kg.). X-ray crystallography confirmed the amorphous nature of the product.

EXAMPLE 3

[R-(R*,R*)-2-4-fluorophenyl)-β,δ-dihydroxy-5-(1-methylethyl)-3-phenyl-4-[(phenylamino)carbonyl)-1H-pyrrole-1-heptanoic acid hemicalcium salt (Amorphous Atorvasatin Calcium)

The process of Example 1 was repeated with crystalline atorvastatin calcium (10 kg) dissolved in tetrahydrofuran (30 lt) and using n-heptane instead of cylcohexane to give amorphous atorvastatin (9.6 kg). X-ray crystallography examination confirmed the amorphous nature of the product.

While the present invention has been described in terms of its specific embodiments, certain modifications and equivalents will be apparent to those skilled in the art and are intended to be included within the scope of the present invention.

We claim:

1. A process for the preparation of amorphous atorvastatin calcium and hydrates thereof which comprises:

(a) dissolving crystalline atorvastatin calcium in a non-hydroxylic solvent;

(b) adding a non-polar hydrocarbon anti-solvent or adding the dissolved atorvastatin to the non-polar anti-solvent to precipitate out atorvastatin calcium; and (c) removing the solvent by filtration to afford amorphous atorvastatin calcium.

2. The process of claim 1, wherein the non-hydroxylic solvent is tetrahydrofuran and anti-solvent is chosen from a group of non-polar hydrocarbon solvents comprising n-hexane, cyclohexane or n-heptane.

3. The process of claim 1, wherein the non-hydroxylic solvent is tetrahydrofuran and anti-solvent is n-hexane.

4. The process of claim 1, wherein the non-hydroxylic solvent is tetrahydrofuran and anti-solvent is cylcohexane.

5. The process of claim 1, wherein the non-hydroxylic solvent is tetrahydrofuran and anti-solvent is n-heptane.

* * * * *